(12) United States Patent
Helmer

(10) Patent No.: US 12,211,604 B2
(45) Date of Patent: Jan. 28, 2025

(54) MEDICAL DEVICE HAVING CAMERA

(71) Applicant: Sanofi, Paris (FR)

(72) Inventor: Michael Helmer, Frankfurt am Main (DE)

(73) Assignee: Sanofi, Paris (FR)

( * ) Notice: Subject to any disclaimer, the term of this patent is extended or adjusted under 35 U.S.C. 154(b) by 931 days.

(21) Appl. No.: 17/293,731

(22) PCT Filed: Nov. 14, 2019

(86) PCT No.: PCT/EP2019/081296
§ 371 (c)(1),
(2) Date: May 13, 2021

(87) PCT Pub. No.: WO2020/104284
PCT Pub. Date: May 28, 2020

(65) Prior Publication Data
US 2022/0013208 A1    Jan. 13, 2022

(30) Foreign Application Priority Data
Nov. 23, 2018  (EP) ..................................... 18306559

(51) Int. Cl.
*G16H 20/17*   (2018.01)
*A61M 5/315*   (2006.01)
(Continued)

(52) U.S. Cl.
CPC ........ *G16H 20/17* (2018.01); *A61M 5/31585* (2013.01); *G06V 20/68* (2022.01);
(Continued)

(58) Field of Classification Search
CPC ... G16H 20/17; G16H 20/60; A61M 5/31585; A61M 2205/52; A61M 2205/583; A61M 2205/587; A61M 2205/60; G06V 20/68
See application file for complete search history.

(56) References Cited

U.S. PATENT DOCUMENTS

2010/0249530 A1    9/2010   Rankers et al.
2012/0316405 A1   12/2012   Taylor
(Continued)

FOREIGN PATENT DOCUMENTS

CN    101536061 A    9/2009
CN    102300501 A   12/2011
(Continued)

OTHER PUBLICATIONS

Machine translation for CN 107077530 (Year: 2017).*
(Continued)

*Primary Examiner* — Qian Yang
(74) *Attorney, Agent, or Firm* — Fish & Richardson P.C.

(57) ABSTRACT

This application relates to medical devices having cameras. According to a first aspect, this specification describes an electronic device comprising: a display; and a stereoscopic camera, in which the electronic device is configured to: capture a stereoscopic image using the stereoscopic camera; determine if the captured stereoscopic image comprises one or more items of food; in the event of a positive determination, determine an estimate of nutritional content of the one or more items of food in dependence on the captured stereoscopic image; and display information relating to the estimate of nutritional content via the display.

16 Claims, 10 Drawing Sheets

(51) Int. Cl.
   *G06V 20/68* (2022.01)
   *G16H 20/60* (2018.01)
(52) U.S. Cl.
   CPC ......... *G16H 20/60* (2018.01); *A61M 2205/52* (2013.01); *A61M 2205/583* (2013.01); *A61M 2205/587* (2013.01); *A61M 2205/60* (2013.01)

(56) References Cited

U.S. PATENT DOCUMENTS

| | | | |
|---|---|---|---|
| 2014/0322682 A1* | 10/2014 | Baym | G09B 5/02 |
| | | | 340/5.6 |
| 2016/0063692 A1 | 3/2016 | Divakaran et al. | |
| 2018/0122063 A1 | 5/2018 | Dehais et al. | |
| 2019/0321545 A1* | 10/2019 | Saint | G16H 40/67 |

FOREIGN PATENT DOCUMENTS

| | | | |
|---|---|---|---|
| CN | 107077530 | * | 8/2017 |
| CN | 107731278 A | | 2/2018 |
| CN | 107845414 A | | 3/2018 |
| CN | 107873101 A | | 4/2018 |
| CN | 107885425 A | | 4/2018 |
| CN | 207216317 | | 4/2018 |
| CN | 108140328 A | | 6/2018 |
| JP | 2015-187870 A | | 10/2015 |
| JP | 2016-512442 A | | 4/2016 |
| WO | WO 2005/089833 A1 | | 9/2005 |
| WO | WO 2008/043043 A2 | | 4/2008 |
| WO | WO 2010/091102 A1 | | 8/2010 |
| WO | WO 2013/123416 A2 | | 8/2013 |
| WO | WO 2014123998 | | 8/2014 |
| WO | WO 2016/081831 A1 | | 5/2016 |
| WO | WO 2017/044161 A1 | | 3/2017 |

OTHER PUBLICATIONS

PCT International Search Report and Written Opinion in International Application No. PCT/EP2019/081296, dated Jan. 1, 2020, 9 pages.
PCT International Preliminary Report on Patentability in International Application No. PCT/EP2019/081296, dated May 25, 2021, 6 pages.

* cited by examiner

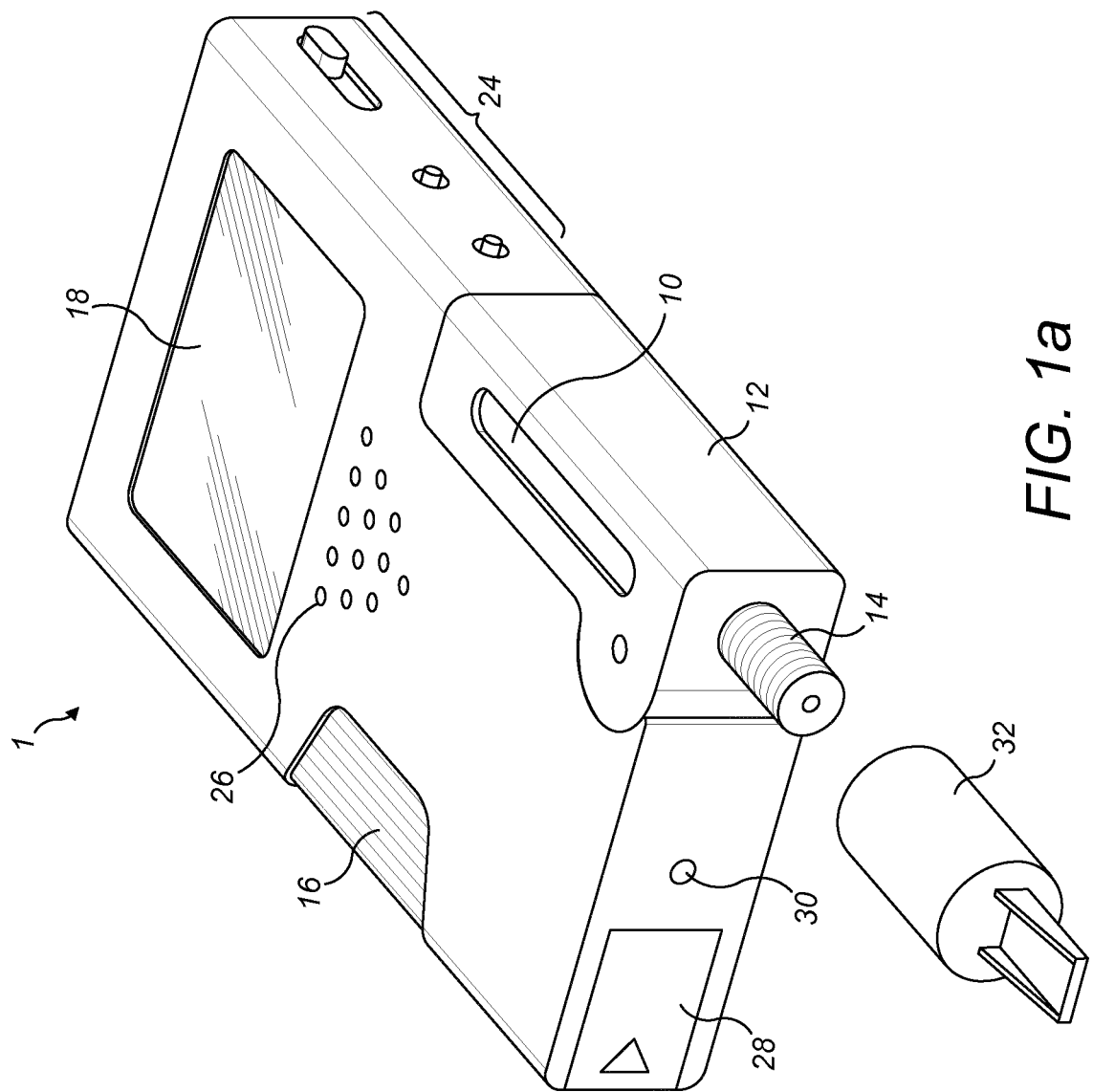

MEDICAL DEVICE HAVING CAMERA

CROSS REFERENCE TO RELATED APPLICATIONS

The present application is the national stage entry of International Patent Application No. PCT/EP2019/081296, filed on Nov. 14, 2019, and claims priority to Application No. EP 18306559.8, filed on Nov. 23, 2018, the disclosures of which are incorporated herein by reference.

TECHNICAL FIELD

This application relates to medical devices having cameras. In particular, this application relates to injection devices having stereoscopic cameras.

BACKGROUND

Injection devices can be used to supply variable doses of medicament to a user. In some situations, a user sets the dose of medicament to be supplied based on nutritional content of food that the user has consumed. For example, a user can set an insulin dose based on the carbohydrate or sugar content of food they have consumed. However, user estimates of nutritional content of the food they have consumed can be inaccurate, resulting in the user setting an incorrect or inappropriate medicament dose.

Furthermore, injection devices may comprise multiple user settings that can be configured in dependence on user requirements or preferences. However, configuring the injection device can prove difficult for some users.

SUMMARY

According to a first aspect, this specification describes an electronic device comprising: a display; and a stereoscopic camera, wherein the electronic device is configured to: capture a stereoscopic image using the stereoscopic camera; determine if the captured stereoscopic image comprises one or more items of food; in the event of a positive determination, determine an estimate of nutritional content of the one or more items of food in dependence on the captured stereoscopic image; and display information relating to the estimate of nutritional content via the display.

Determining if the captured stereoscopic image comprises one or more items of food may comprise partitioning the stereoscopic image into a plurality of segments based on visual and/or spatial properties of the stereoscopic image.

Determining an estimate of nutritional content of the one or more items of food may comprise identifying the one or more of the items of food. Identifying the one or more of the items of food may comprise using an image recognition algorithm.

Determining an estimate of nutritional content of the one or more items of food may comprise providing a plurality of selectable options for identifying the one or more items of food.

Determining an estimate of nutritional content of the one or more items of food may comprise using a lookup table.

The nutritional information may comprise an estimate of carbohydrate content of the one or more items of food.

The electronic device may be an injection device comprising an expulsion mechanism for expelling medicament from the injection device. The electronic device may be further configured to adjust an amount of medicament to be expelled from the injection device by the expulsion mechanism. The amount of medicament to be expelled from the injection device by the expulsion mechanism may be set based on the estimated nutritional content of the one or more items of food.

The device may be further configured to: capture an image of a visual code associated with a prescription using the stereographic camera; and configure one or more settings of the injection device in dependence on the captured image of the visual code. Configuring the one or more settings of the injection device may comprise: connecting the injection device to a network in dependence on the captured image of the visual code; and transferring data to the injection device via the network. The one or more settings may comprise at least one of: a user identity; user details; an identity of a medical professional; a registration number of a medication batch; an identity of a medication; medication administration policies; and/or a user history.

The electronic device is may be further configured to: capture a visual code associated with a medicament; and register an amount of medicament available in dependence on the captured visual code.

The electronic device may comprise a medicament cartridge comprising a medicament.

BRIEF DESCRIPTION OF THE FIGURES

Example embodiments will now be described by way of non-limiting example with reference to the accompanying drawings, in which.

As used herein, the term "food" is preferably used to connote both food and drink.

DETAILED DESCRIPTION

Figure 1B:
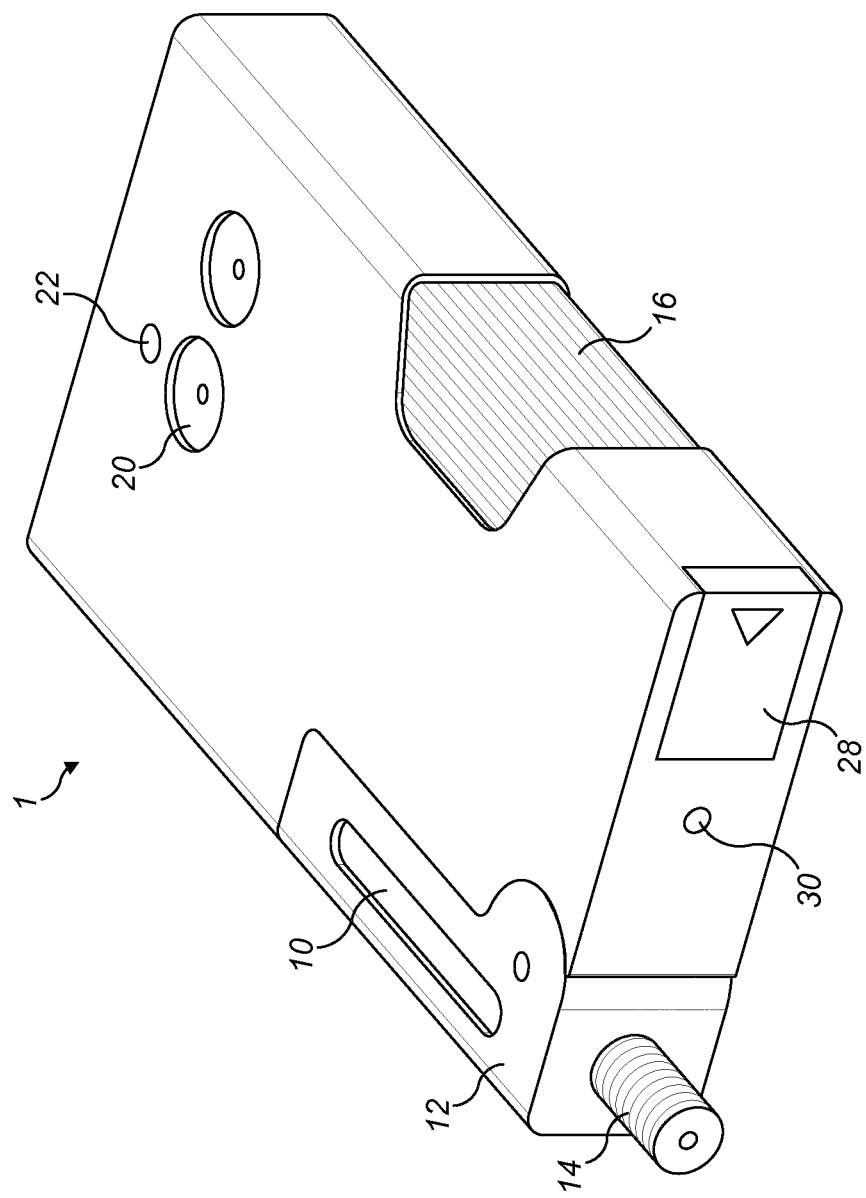
FIG. 1b shows a rear view an injection device.

FIGS. 1A and 1B shows an example of an injection device having a stereoscopic camera. While features will be described with reference to an injection device, in alternative embodiments other electronic devices, for example smart phones and/or tablets, can be used to perform some of the functions described below.

The injection device 1 comprises a medicament cartridge holder 12 for retaining a medicament cartridge 10. The medicament cartridge 10 is a consumable part of the injection device 1. The medicament cartridge 10 is retained within a medicament cartridge holder 12, from which the medicament cartridge 10 can be removed and a different medicament cartridge 10 inserted. An expulsion mechanism (as described, for example, in relation to FIG. 2 below) can act to dispel medicament from the medicament cartridge 10 via a needle hub/tip 14 in response to an activation signal. The medicament cartridge 10 contains a medicament.

The injection device further comprises an injection button 16. The injection button 16 can be used to provide an activation signal to initiate expulsion of medicament from the medicament cartridge 10 by the expulsion mechanism. In other embodiments, such as the embodiment shown, the injection button 16 is provided as a separate button.

The injection device 1 further comprises a display 18. Optionally the display 18 has touch screen capability. The display 18 can provide a visual indication of the status of the apparatus, such as a mode the apparatus is in, a battery status, and/or whether a power supply is connected. The display can also be used to communicate messages to the user. The display can be in the form of a Liquid Crystal Display (LCD) or Light Emitting Diode (LED) or OLED screen or similar.

In some embodiments, the display 18 may include touch screen functionality, allowing the display 18 to receive user inputs. The touch screen functionality can be used to support installation and troubleshooting procedures. Alternatively or additionally, the display may be accompanied by one or more push buttons or keys in the vicinity of the display, allowing the user to interact with the injection device 1, for example by navigating a cursor through a collection of menus and options on the display.

The injection device further comprises a stereoscopic camera 20. In the example shown, the stereoscopic camera 20 is provided on the opposite face of the injection device 1 to the display 18, as illustrated in FIG. 1*b*. However, in other embodiments, the camera may be provided on any of the other faces of the injection device 1. The stereoscopic camera 20 can capture images that include depth information. The captured images can be displayed via the display 18. In some embodiments, images are displayed on the display 18 during the capture process to guide the user. In the embodiments shown, the stereoscopic camera 20 comprises two camera lenses, though in general other types of stereoscopic camera 20 can be used.

In some embodiments, the stereoscopic camera 20 is provided with a camera light/flash 22 for illuminating scenes in low light levels. The camera light 22 may operate independently of the stereoscopic camera 20. The camera light 22 may provide continuous short illumination.

A user of the injection device 1 can use the stereoscopic camera 20 to capture images of items of food and/or drink that the user intends to consume. The injection device is configured to recognise one or more items of food and/or drink in the captured image. The injection device 1 is further configured to estimate nutritional content of the identified one or more items of food and/or drink. Nutritional content may comprise the carbohydrate content of the one or more items of food. Nutritional content may alternatively or additionally comprise one or more of: fat content; cholesterol content; vitamin content; mineral content; and/or fiber content. Other examples are possible.

The use of a stereographic camera 20 to capture images of items of food and/or drink can result in a more accurate determination of the nutritional content of the food and/or drink. For example, the volume of the food and/or drink can be more accurately determined by using depth information. Furthermore, a stereoscopic image of the items of food and/or drink can allow more accurate identification of the items of food and/or drink.

The estimated nutritional content can be displayed to the user via the display 18 of the injection device 1. The display 18 can, in some embodiments, further display a recommended medicament dose based on the estimated nutritional content. In some embodiments, the injection device 1 can also vary a dose of medicament to expelled from the injection device in dependence on the estimated nutritional content.

In some embodiments, the nutritional content-estimation functions may alternatively be provided by an application running on an electronic device equipped with a stereoscopic camera. Examples of such a device include: a smartphone; a tablet; and/or a laptop.

A method of determining items of food present in a captured image and nutritional content of the items of food is described in more detail below in relation to FIGS. 4, 5A and 5B.

The injection device further comprises a control panel 24. The control panel may comprise one or more of: a power switch (i.e. on/off switch); a release switch for the cartridge holder 12; dose setting buttons; controls for the display 18 and/or controls for the camera 20.

The injection device 1 may further comprise a speaker 26 for transmitting audio signals to the user in the form of sound. The injection device may further comprise a microphone (not shown) for receiving user inputs in the form of sound.

The injection device 1 may be powered by a battery 28. The battery 28 can be provided in the form of a rechargeable battery. A power port 30 may also be provided on the injection device 1 for supplying external power to the injection device 1. The power port 30 can, in some embodiments, also be used to recharge the battery 28.

In some embodiments, the injection device comprises a removable cap 32 for protecting the needle hub 4.

Figure 1C:
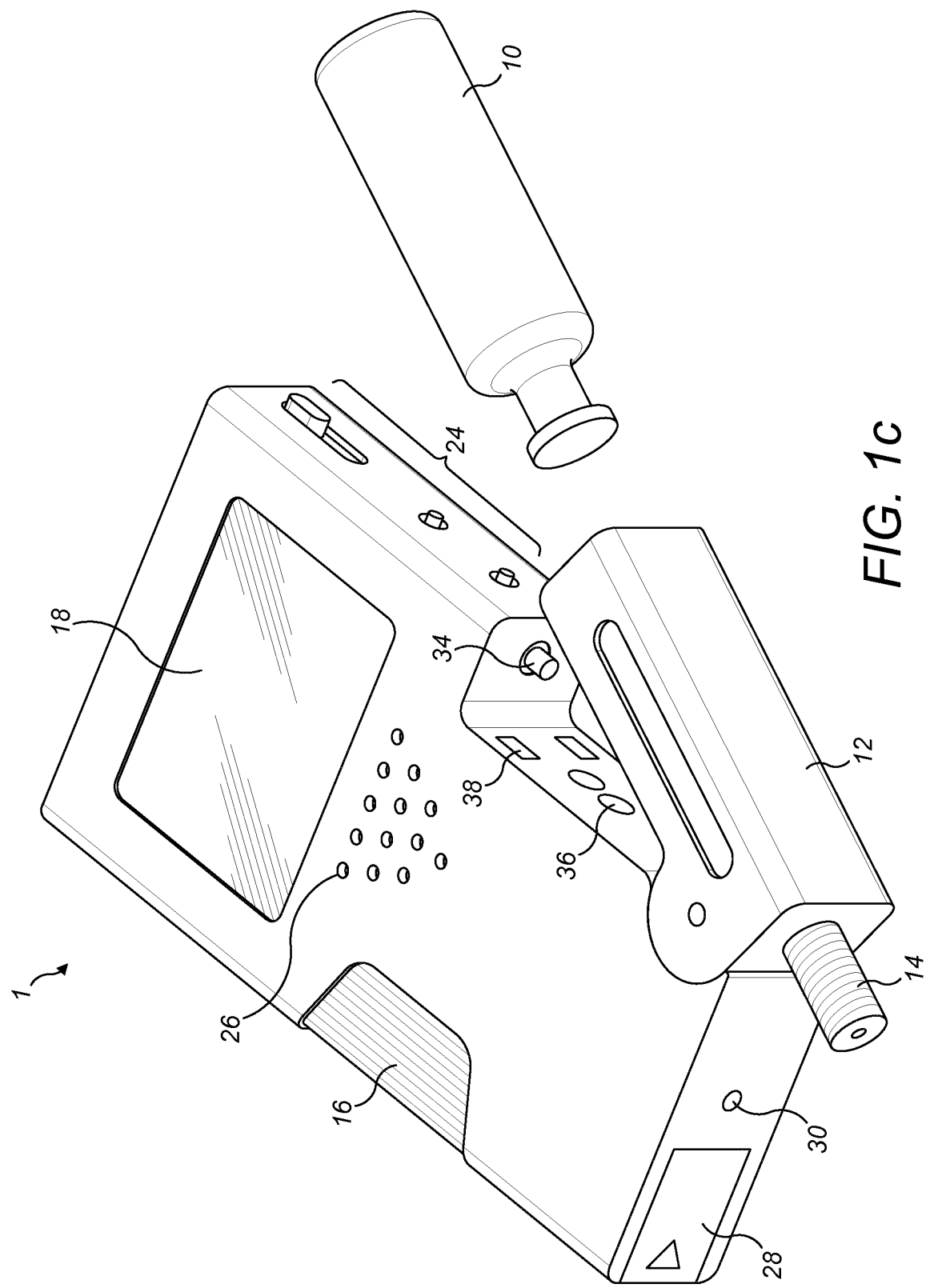
FIG. 1c shows a front view of an injection device with the medicament cartridge removed.

FIG. 1C shows a front view of an example of an injection device with the medicament cartridge 10 removed.

The medicament cartridge 10 can be removed from the cartridge holder 12. The cartridge holder 12 can be hinged from the main body of the injection device 1, as shown in FIG. 1*c*. This allows easy and convenient retention and removal of the medicament cartridge 10 from the injection device. The cartridge holder 12 may be retained in place by a latch 38.

The injection device 1 further comprises a plunger 34 for displacing a stopper 35 within the medicament cartridge 10 in order to expel medicament from the injection device. The plunger 34 may form a part of the expulsion mechanism.

In some embodiments, the injection device 1 further comprises a scanner 36. The scanner 36 may be in the form of an optical CCDM unit. The scanner 36 is configured to monitor optical codes on medicament cartridges 10 to register individual medicament cartridges. For example, the scanner 36 may record a LOT number of the medicament cartridge 10. This can be important for re-using individual medicament cartridges 10.

The scanner 36 can, in some embodiments, also be used to monitor one or more of: a medicament colour; and/or a medicament level in the medicament cartridge 10.

Figure 1D:
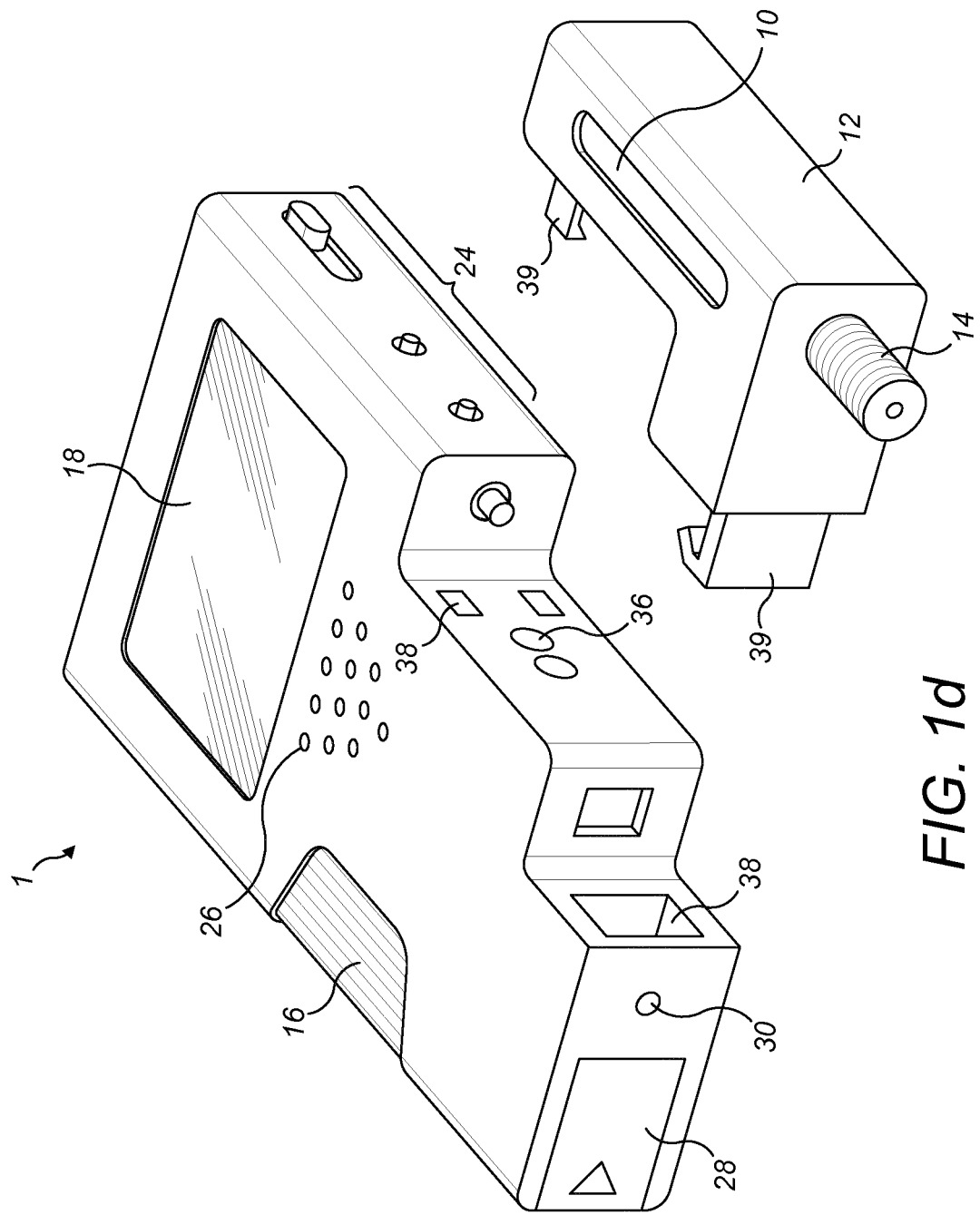
FIG. 1a shows a front view an injection device.

FIG. 1D shows a front view of an example of an injection device with a changeable cartridge holder. In some embodiments, the injection device 1 has a changeable cartridge holder 12. This allows the injection device 1 to be used with different types of medicament cartridge 10. For example, the injection device 1 can be used with both short and/or long acting insulin during the treatment in-use time. The injection device 1 evaluates the correct cartridge holder, for example using the scanner 36. In the embodiment shown, the cartridge holder 12 comprises a plurality of "latch snaps" 39 that interact with latches 38 to retain the cartridge holder 12 with the injection device 1. Use of removable cartridge holders can protect the medicament cartridge 10 during installation of the medicament cartridge 10. For example, if the medicament cartridge 10 is a glass cartridge, the removable cartridge holder 12 can act to reduce glass breakage during installation.

Figure 2:
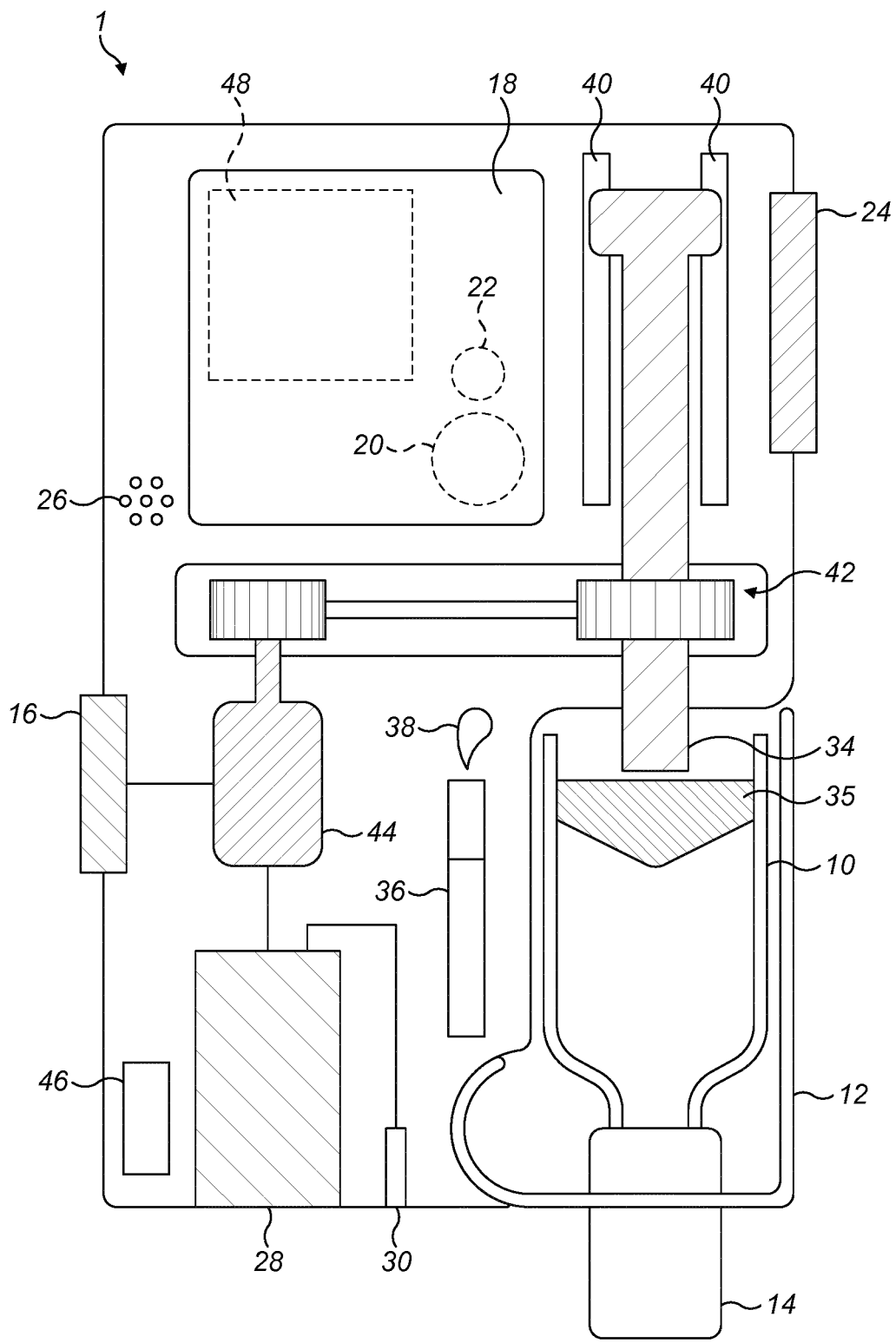
FIG. 2 shows a schematic diagram of an injection device, including internal features.

FIG. 2 shows a schematic diagram of an injection device, including internal features.

In the embodiment shown, the expulsion mechanism comprises a plunger 34 comprising a dovetail that is retained within slits 40 in the injection device 1. The expulsion mechanism comprises a free of play timing belt drive 42 to drive the plunger 34. A motor 44 provides drives the free of play timing belt drive 42. Guidance of the piston rod in rotatory direction is provided via the housing using the dovetail guide slits 40. The motor 44 may comprise an absolute rotation sensor and/or a stepper motor for controlling the number of rotations of the motor 44. The piston position of the plunger 34 relative to the cartridge can, in some embodiments, be determined from the number of motor 44 revolutions. In some embodiments, the absolute position of the plunger is determined by a scanner 36 unit when the cartridge is installed. In some embodiments, the scanner unit 36 determines a required plunger stroke by measuring the medicament level in the medicament cartridge 10. The motor 44 can use the required plunger stroke to provide a number of rotations that will provide that plunger stroke, such that the requisite plunger position in the medicament cartridge 10 is reached. The motor system may also be provided with an absolute value for the plunger 34 to stopper 35 distance before the injection device is first used. This can ensure that the motor displaces the plunger by the correct distance to expel the required amount of medicament, and help prevent too little or too much medicament being expelled.

A network interface 46 is also provided on the apparatus in order to connect apparatus to a network. The interface may be provided, for example, by one or more of: a Wi-Fi interface; an Ethernet interface; a Bluetooth transceiver; and/or a USB interface. The apparatus can connect to a local area network (LAN) and/or the Internet via the network interface 46, allowing it to exchange data with other members of the network. The apparatus may also use the network interface to connect directly with additional devices, using, for example, a Bluetooth connection.

The apparatus can be connected to a data server via the network interface 46. The data server may comprise a nutritional database. Through this connection the apparatus can share data in a bi-directional manner with the data server. The data server can be remotely located from the apparatus, for example at a data centre controlled by a medicine supplier or a device manufacturer. Alternatively, the data centre can be part of a distributed computer system, such as "the cloud". In some embodiments, the data server may be located locally to the apparatus on the same Local Area Network.

Components of the injection device, such as the motor 44, network interface 46, stereographic camera 20, display 18, speaker/microphone 26 and controls 24 for example, are controlled by a control system (not shown). The control system can sens and receive electronic signals to and from components it is connected to.

The injection device 1 further comprises an electronics system comprising a processor arrangement 48. The electronics system is used to control and perform functions of the injection device 1, as described below. The control system described above comprises several of the components of the electronics system, including the processor arrangement 48 and associated memories 50, 52.

Figure 3:
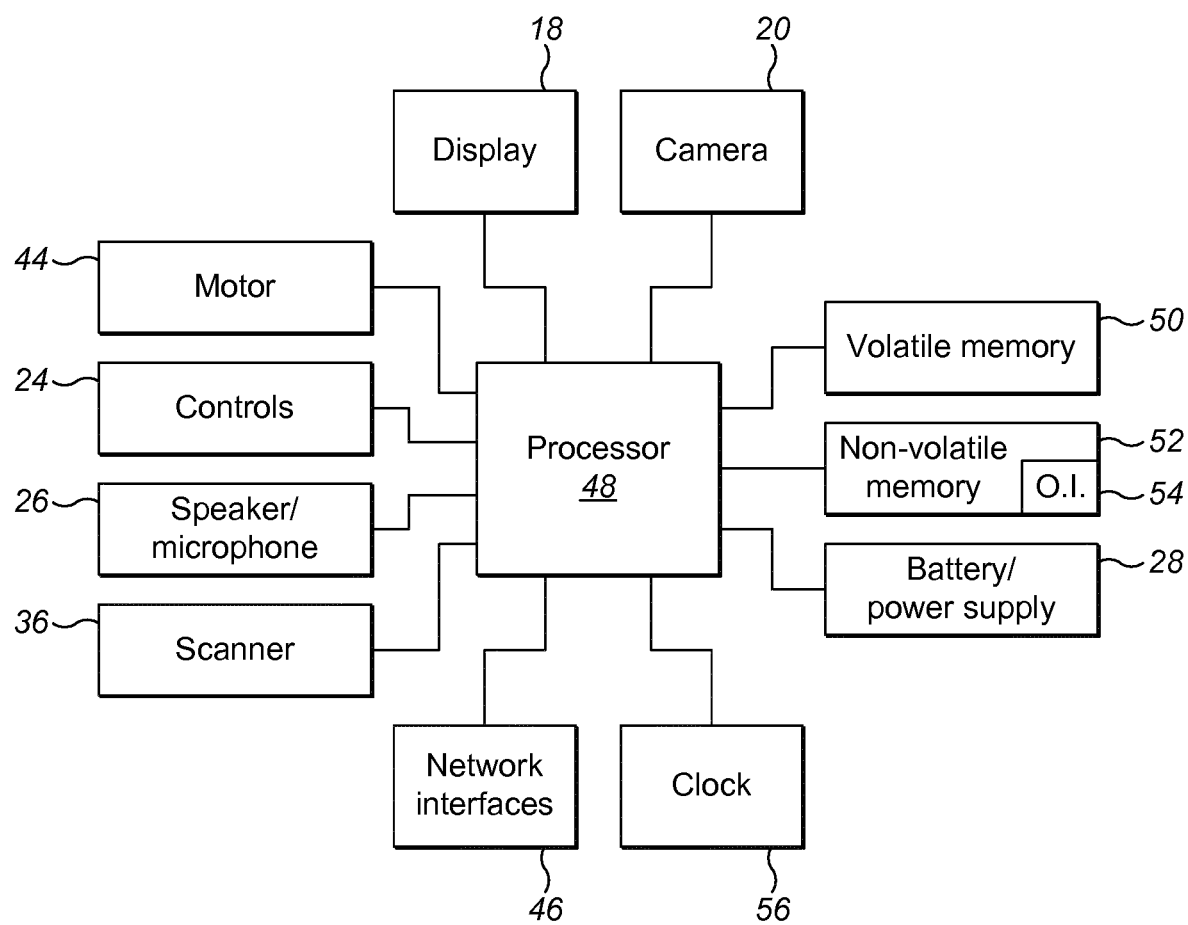
FIG. 3 shows a schematic diagram of an electronics system of an injection device.

With respect to FIG. 3, a schematic representation of an example of an electronics system of the injection device is shown. The electronics system comprises the processor arrangement 48. The processor arrangement 48 and other hardware components may be connected via a system bus (not shown). Each hardware component may be connected to the system bus either directly or via an interface. A power supply 28 is arranged to provide power to the electronics system. In some embodiments a battery may also be provided to enable the use of the apparatus without a power connection to the mains supply. Said battery may be rechargeable.

The processor arrangement 48 controls operation of the other hardware components of the electronics system. The processor arrangement 48 may be an integrated circuit of any kind. The processor arrangement 48 may for instance be a general purpose processor. It may be a single core device or a multiple core device. The processor arrangement 48 may be a central processing unit (CPU) or a general processing unit (GPU). Alternatively, it may be a more specialist unit, for instance a RISC processor or programmable hardware with embedded firmware. Multiple processors may be included. The processor arrangement 48 may be termed processing means.

The electronics system comprises a working or volatile memory 50. The processor arrangement 48 may access the volatile memory 50 in order to process data and may control the storage of data in memory. The volatile memory 50 may be a RAM of any type, for example Static RAM (SRAM), Dynamic RAM (DRAM), or it may be Flash memory (e.g. SD-Card). Multiple volatile memories may be included, but are omitted from the Figure.

The electronics system comprises a non-volatile memory 52. The non-volatile memory 52 stores a set of operation instructions 54 for controlling the normal operation of the processor arrangement 48. The non-volatile memory 52 may be a memory of any kind such as a Read Only Memory (ROM), a Flash memory or a magnetic drive memory. Other non-volatile memories may be included, but are omitted from the Figure.

The processor arrangement 48 operates under the control of the operating instructions 54. The operating instructions 54 may comprise code (i.e. drivers) relating to the hardware components of the electronics system, as well as code relating to the basic operation of the apparatus. The operating instructions 54 may also cause activation of one or more software modules stored in the non-volatile memory 52. Generally speaking, the processor arrangement 48 executes one or more instructions of the operating instructions 54, which are stored permanently or semi-permanently in the non-volatile memory 52, using the volatile memory 50 temporarily to store data generated during execution of the operating instructions.

The processor arrangement 48, the volatile memory 50 and the non-volatile memory 52 may be provided as separate integrated circuit chips connected by an off-chip bus, or they may be provided on a single integrated circuit chip. The processor arrangement 48, the volatile memory 50 and the non-volatile memory 52 may be provided as a microcontroller.

The electronics system comprises a clock 56. The clock 56 may be a clock crystal, for example, a quartz crystal oscillator. The clock 56 may be a separate component to the processor arrangement 48 which is configured to provide a clock signal to the processor arrangement 48. The processor arrangement 48 may be configured to provide a real time clock based on the signal from the clock 56. Alternatively, the clock 56 may be a clock crystal which is provide on a single integrated circuit chip with the processor arrangement 48. Other possibilities can be the implementation of a radio controlled clock or time adjustment by internet connection.

The electronics system comprises one or more network interfaces 46. The network interfaces 46 facilitate the connection of the injection device to one or more computer networks and the bi-directional exchange of information between the injection device and other members of the networks. These networks may include the Internet, a Local Area Network, or any other network required by the apparatus to communicate with the data centre and/or contact centre. The network interfaces 46 comprise a network interface controller, such as an Ethernet adaptor, a Wi-Fi adaptor and/or a Bluetooth adaptor. The network interfaces 46 are associated with one or more network addresses for identifying the injection device on the network. The one or more network addresses may be in the form of an IP address, a MAC address, and/or an IPX address.

In some embodiments, the electronic system comprises a microphone 26. The microphone 26 can be operated to receive an input in the form of a sound, and to convert said sound into an electronic audio signal capable of being processed in the digital domain.

The processor arrangement 48 can, in some embodiments, be configured to detect command in audio signals detected by the microphone. The processor 48 may implement a speech-to-text algorithm in order to convert the audio signal into a natural language stream. Such algorithms can include Hidden Markov Models, Dynamic Time Warping, or Neural Networks. The processor arrangement 48 may be further configured to analyse the natural language data stream in order to determine if a voice command is present in the natural language data stream. The processing arrangement 48 can achieve this by identifying potential voice commands in the natural language data stream and assigning to each of the potential voice commands a confidence level.

The electronics system also comprises a speaker 26. The speaker 26 is an example of an audio transducer. The speaker 26 can be operated to provide an audio output in the form of spoken word, or more generally any sound. The processor arrangement operates the speaker to provide an audio output based on responses received from the medical database and/or on conditions present in the operating instructions of the processing arrangement.

The electronics system may comprise a display driver. The display driver may be provided as a separate integrated circuit chip to the processor arrangement, which is connected by an off-chip bus. Alternatively, the display driver may be provided on a single integrated circuit chip with the processor arrangement.

The electronics system comprises a display 18 for displaying a user interface. The display 18 can be operated by the processing arrangement 48 via a display driver to provide one or more visual notifications to a user. The display 18 can provide a visual indication of the status of the injection device, such as which mode the injection device is in, a battery status, and/or whether a power supply is connected. The display 18 may also display images captured by the camera 20.

The processor arrangement 48 may check the state of charge of one or more batteries. If the state of charge is determined to be low, the display may be operated to show a battery low warning.

In some embodiments, the processor arrangement 48 in the injection device may not be sufficiently powerful to perform one or more of the functions described herein. Instead, the processing arrangement 48 is configured to communicate via the network interface 46 with an additional computer system that has more computing power available to it. The processor arrangement 48 can transmit data from the apparatus to the additional computer system, where it can be processed using the additional computing power of the additional computer system. The additional computer system can return the results of this processing back to the processor arrangement 48 for further processing. The additional computing system can, for example, be a remote computer system, a distributed computer system, or part of a data centre.

Figure 4:
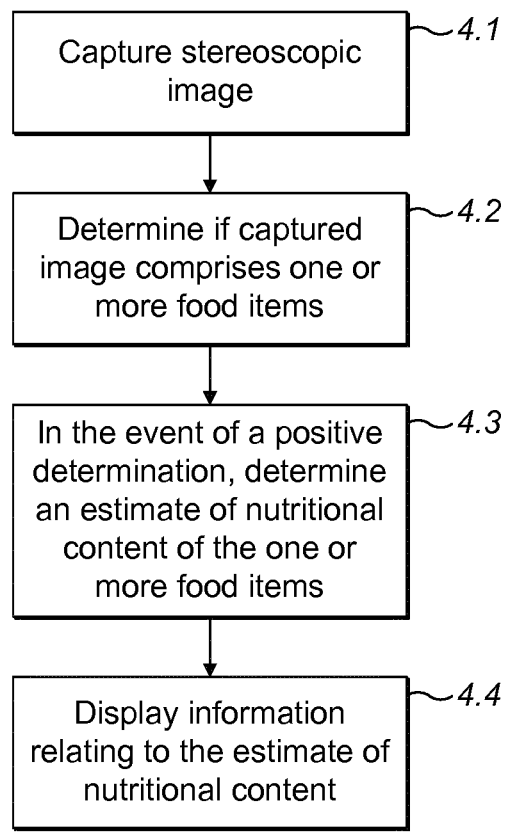
FIG. 4 shows a flow diagram of a method using an injection device.

FIG. 4 shows a flow diagram of a method of analyzing captured images to determine nutritional information.

At operation 4.1, a stereoscopic image is captured by the stereoscopic camera 20 of the injection device 1. In some embodiments, in low light conditions, a flash 22 can be used to illuminate the scene being captured by the camera 20.

At operation 4.2, it is determined if the captured image comprises one or more food items. An image recognition algorithm can be used to identify food and/or drink items in the captured image.

At operation 4.3, if the captured image is determined to comprise one or more food items, an estimate of the nutritional content of the one or more food items in the captured image is determined. In some embodiments, the nutritional content is the carbohydrate content of the food in the captured image. Other examples include one or more of: fat content; cholesterol content; fiber content; vitamin content; mineral content; and/or salt content.

In some embodiments, the estimated nutritional content can be determined using a look-up table. The injection device 1 may be configured to estimate the volume each of the identified types of food. Based on the volume and the type of food, the nutritional content can be estimated. Using a stereoscopic image to estimate the volume of food items can result in a more accurate estimate of the food item volume (and therefore nutritional content) when compared to a flat image, or an image having no stereoscopic information.

At operation 4.4, the estimate of the nutritional content is output via the display 18 on the injection device 1. The injection device may further output a recommended medicament dose based on the estimated nutritional content via the display. For example, an insulin dose may be presented to the user via the display. The insulin dose may be based on the estimated carbohydrate content of the food. The insulin dose may be short-term insulin dose.

In some embodiments, the estimate of the nutritional content can be used to adjust the dose of medicament expelled from the injection device. For example, an insulin dose may be set based on the estimated carbohydrate content of the food.

Figure 5B:
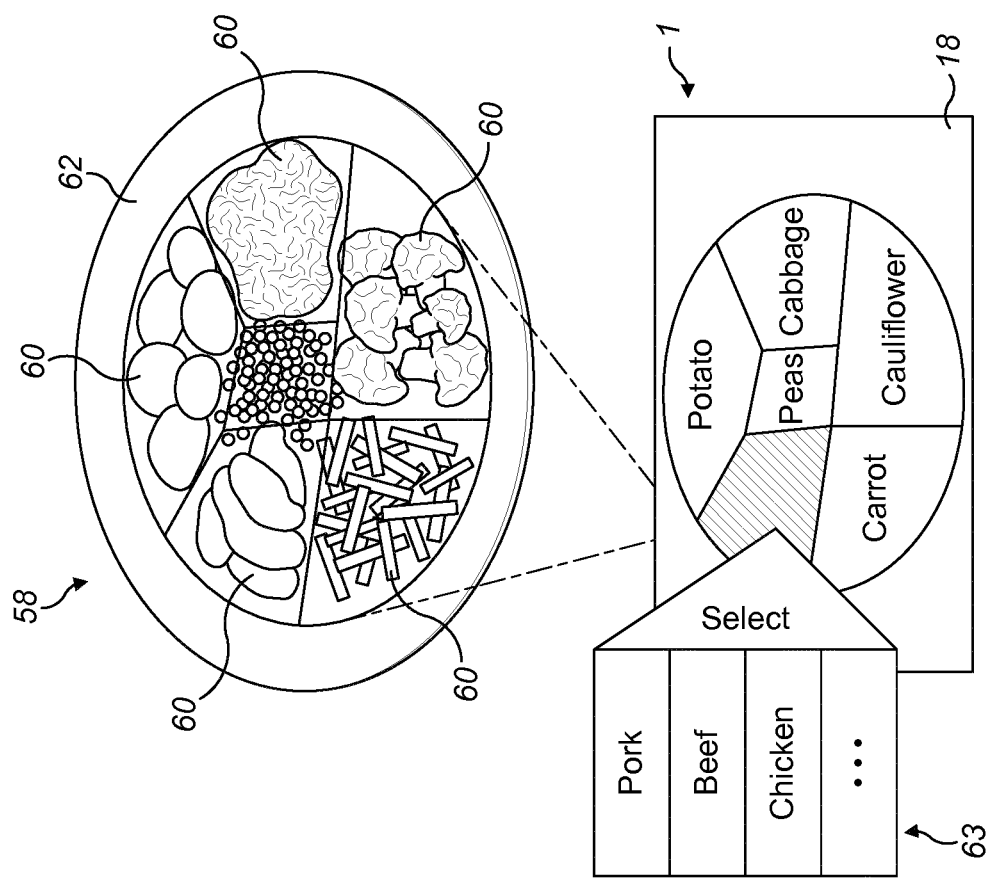
FIGS. 5A and B show examples of methods for identifying food in a captured image.
Figure 5A:
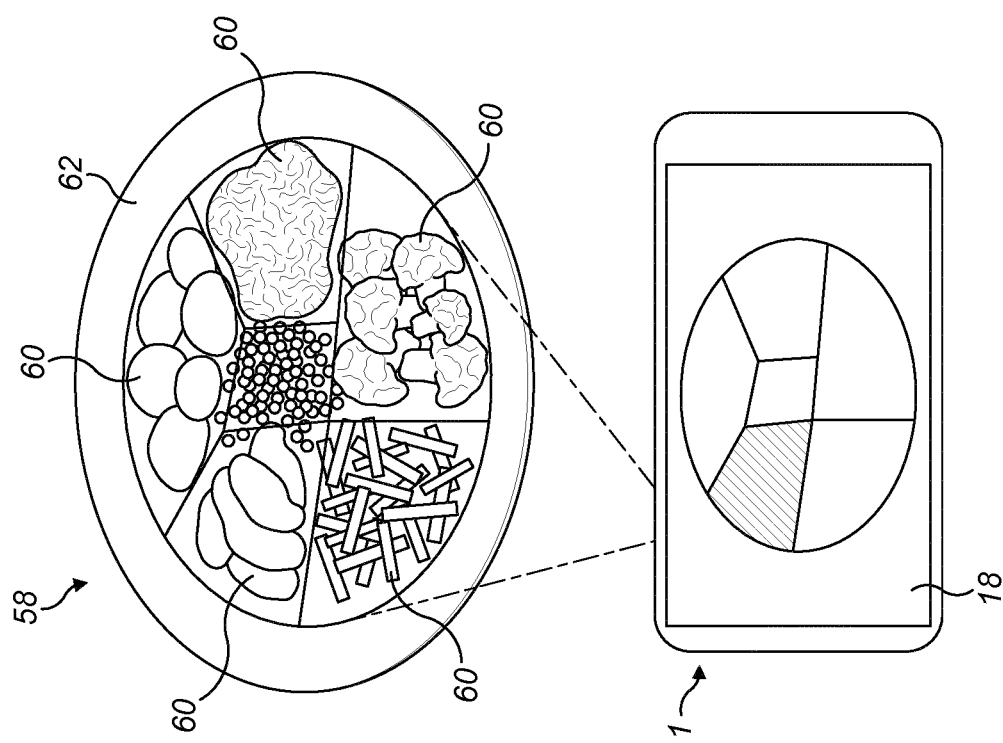

FIGS. 5A and B show examples of methods for identifying food in a captured image. In some embodiments, when the user takes a picture from food with the steroscopic camera, the injection device application can calculate the weight from the picture and recognize the kind of food using a data base. When the data base has no unambiguous assignment the user can specify the ambiguous part of the image. In some embodiments, the device can calculate nutritional content by means of an online nutrition table In FIG. 5A, a captured image the stereoscopic image is partitioned into a plurality of segments based on visual properties of the segments 60. An image segmentation algorithm can be used to partition the image. The volume of the food items contained in each segment is estimated. In some embodiments, a plate 62 can be used align the image and/or provide a scale for the image.

In FIG. 5B, each segment is associated with one or more food items. An image recognition algorithm can be used to identify the food item or items in each segment 60. In some embodiments, the image recognition algorithm assigns a confidence score to food identities based on the image content of a segment in order to identify the food contained in that segment. If the confidence score for a food type exceeds a threshold value, them that segment is identified as being that food type. In some embodiments, if a plurality of food type confidence scores exceed the threshold value, a selectable list 63 is displayed on the display 18 of the injection device 1. The user can select the correct food identity from the list 63.

If the threshold value of the confidence score is not met, then in some embodiments the user can be provided with a selectable list 62 to identify the food type.

Based on the identity of the food types in the image, nutritional content of the food in the image is determined. In some embodiments, nutritional content for the whole image is displayed to the user via the display 18. In some embodiments, nutritional content for each of the segments is alternatively or additionally displayed to the user via the display 18.

In some embodiments, the user can override an identification of the food type to correct errors in the image recognition process.

Additionally, or alternatively, the camera functionality of the injection device can be used to provide further features to the injection device. Examples of such functions will now be described with reference to FIGS. 6 and 7.

Figure 6:
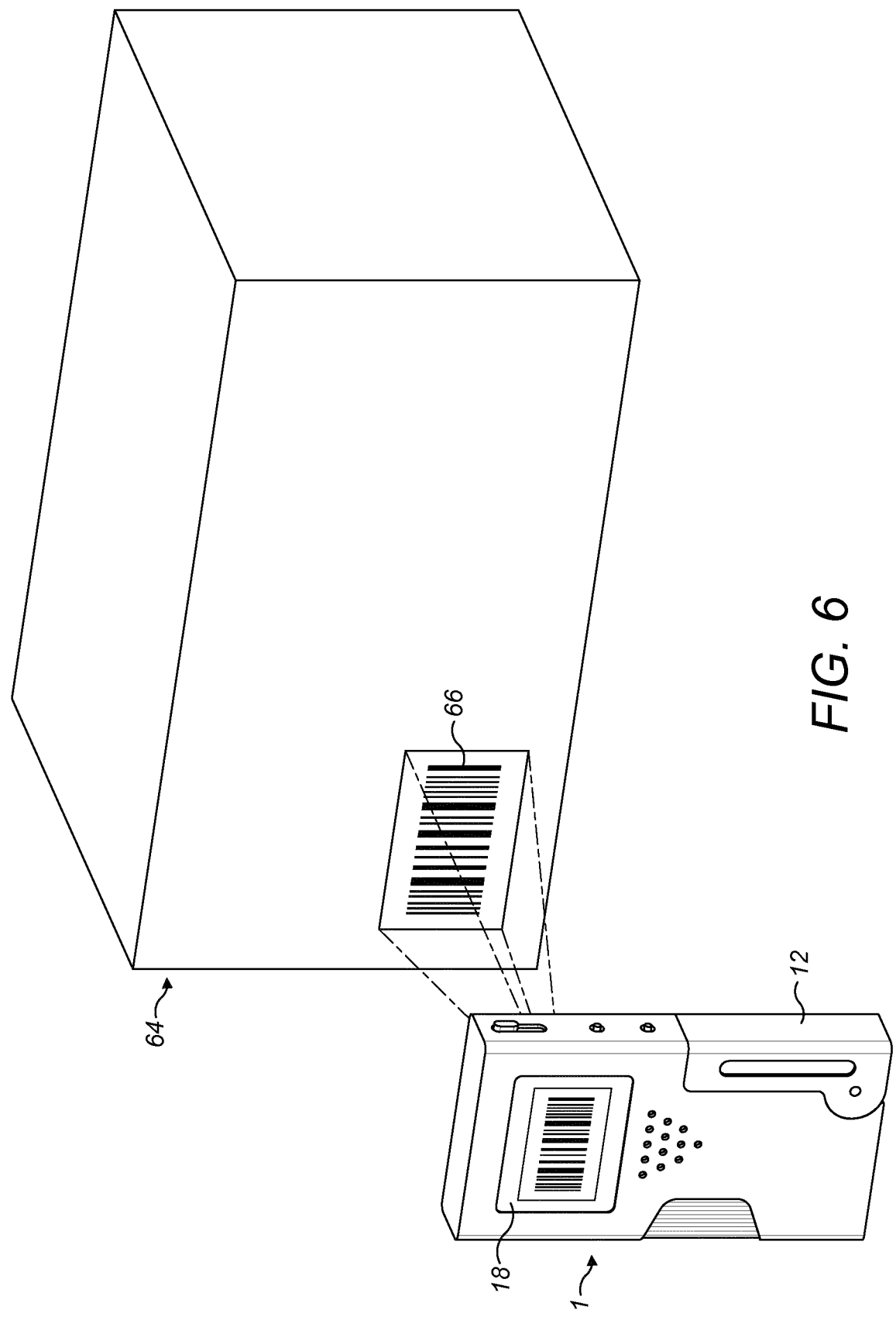
FIG. 6 shows a method of registering a medicament using an injection device.

FIG. 6 shows an example of a method of registering medicament using the injection device camera. One example of an additional feature that the stereoscopic camera 20 can provide for the injection device 1 is the registration of medication available to a user. A visual code 66 may be provided on a container 64 that contains one or more medicament cartridges and/or medicament supplies. Alternatively or additionally, the visual code 66 may be provided on a prescription and/or pharmacy receipt.

The camera 20 can be used as a code reader to read the visual code 66. The visual code may comprise information relating to the contents of the container 64 or prescription to which it relates. For example, the visual code 66 may comprise one or more of: a medicament identity and/or type; a medicament batch; a medicament use-by date; and/or a medicament quantity. The medicament quantity can be used to monitor the available medicament over time. For example, the injection device can keep track of the medicament quantity registered with the device and the amount of medicament used by the device (for example, using the scanner 36). The injection device can use this information to determine when further supplies of the medicament should be ordered. The user may be presented with the instructions to order more medicament supplies via the display 18 of the injection device 1. Alternatively or additionally the injection device may automatically initiate an order for more medicament supplies when the injection device 1 detects that medicament stocks are low.

Figure 7:
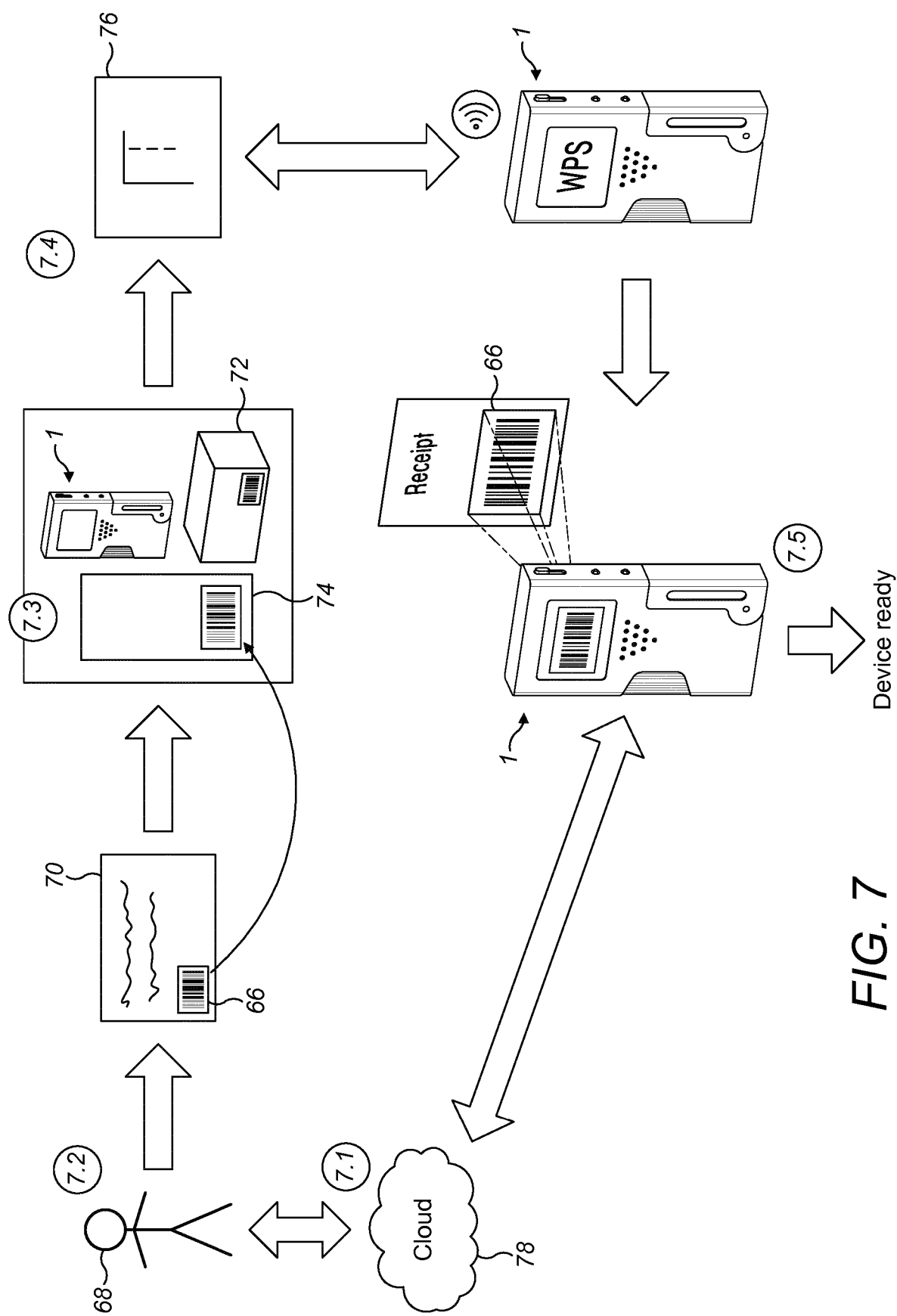
FIG. 7 a method of configuring an injection device using visual codes.

FIG. 7 shows an example of a method of configuring an injection device using the injection device camera. A further example of an additional feature that the stereoscopic camera 20 can provide for the injection device 1 is to assist in configuring the injection device 1.

At operation 7.1, a medical professional 68 registers a user in a database. The user details can, for example, be stored in a distributed database, for example in the cloud 78.

At operation 7.2, the medical professional 68 prepares a user prescription 70. The user prescription 70 is associated with the registered user. The user prescription 70 is associated with visual code 66 that links the prescription to user data in the database. For example, the visual code may represent a log-in code and user name.

At operation 7.3, medicament supplies 72 are supplied to the user, along with the visual code 66. The visual code 66 may be printed, for example, on the medicament supplies 72 and/or a prescription receipt 74. In some examples, the user is also supplied with an injection device 1.

At operation 7.4, the user connects the injection device 1 to a network. For example, the user may connect the injection device 1 to the internet via a router 76. Other methods of connecting the device to the internet are also possible.

At operation 7.5, the user uses the injection device 1 to capture an image of the visual code 66. The visual code links the injection device 1 to the database, for example in the cloud 78. Data transfer is initiated between the database and the injection device 1 based on the contents of the visual code. The injection device 1 downloads one or more items of data from the database in dependence on the visual code 66. The data can, for example, be used to configure the settings of the injection device 1.

In some embodiments, the download of data from the database to configure the injection device 1 can be performed in a pharmacy prior to the user receiving the injection device 1.

The visual code 66 may, in some embodiments, comprise data to connect "barrier-free" the cloud. For example, the visual code 66 may comprise one or more of: a user name; a user identifier; a user login; a link to the database; and/or a user password.

The database comprises user data. Examples of user data included in the database may comprise one or more of: a user name; a user date of birth; a user address; an identity of one or more medical professionals associated with the user (for example a doctor name and/or registration number); one or more medicament identities; one or more medicament administration policies (for example a Long-Term value/Recommendation for short-term value); and/or a user history.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Languatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. An electronic device comprising:
   an injection device comprising an expulsion mechanism for expelling medicament from the injection device;
   a display; and
   a stereoscopic camera,
   wherein the electronic device is configured to:
      capture a stereoscopic image using the stereoscopic camera;
      determine if the captured stereoscopic image comprises one or more items of food;
      in response to the determining that the captured stereoscopic image comprises the one or more items of food, determine an estimate of nutritional content of the one or more items of food based on the captured stereoscopic image, and display information relating to the estimate of nutritional content via the display;
      capture an image of a visual code associated with a prescription using the stereoscopic camera;
      configure medication administration policies of the injection device in dependence on the captured image of the visual code; and
      adjust an amount of medicament to be expelled from the injection device by the expulsion mechanism, wherein the amount of medicament to be expelled from the injection device by the expulsion mechanism is set based on the estimate of nutritional content of the one or more items of food and the medication administration policies.

2. The electronic device of claim 1, wherein the stereoscopic camera comprises a camera light for illuminating scenes in low light levels.

3. The electronic device of claim 1, wherein the estimate of nutritional content comprises an estimate of carbohydrate content of the one or more items of food.

4. The electronic device of claim 1, wherein the nutritional content of the one or more items of food comprises at least one of carbohydrate content, fat content, cholesterol content, vitamin content, mineral content, or fiber content.

5. The electronic device of claim 1, wherein the electronic device is further configured to display, via the display, a recommended medicament dose based on the estimate of the nutritional content.

6. The electronic device of claim 1, wherein the injection device comprises an injection button configured to provide an activation signal to initiate expulsion of medicament from the injection device.

7. The electronic device of claim 1, wherein configuring the one or more settings of the injection device comprises:
   connecting the injection device to a network based on the captured image of the visual code; and
   transferring data to the injection device via the network.

8. The electronic device of claim 1, wherein the one or more settings comprises at least one of: a user identity; user details; an identity of a medical professional; a registration number of a medication batch; an identity of a medication; medication administration policies; or a user history.

9. The electronic device of claim 1, wherein the electronic device comprises a medicament cartridge comprising a medicament.

10. The electronic device of claim 9, wherein the electronic device comprises a scanner configured to monitor an optical code on the medicament cartridge to register the medicament cartridge.

11. The electronic device of claim 1, wherein the electronic device is further configured to:
  capture a visual code associated with a medicament; and
  register an amount of medicament available based on the captured visual code.

12. The electronic device of claim 1, wherein determining if the captured stereoscopic image comprises one or more items of food comprises partitioning the stereoscopic image into a plurality of segments based on visual and/or spatial properties of the stereoscopic image.

13. The electronic device of claim 12, wherein determining an estimate of nutritional content of the one or more items of food comprises identifying the one or more items of food.

14. The electronic device of claim 13, wherein identifying the one or more items of food comprises using an image recognition algorithm.

15. The electronic device of claim 12, wherein determining an estimate of nutritional content of the one or more items of food comprises providing a plurality of selectable options for identifying the one or more items of food.

16. The electronic device of claim 12, wherein determining an estimate of nutritional content of the one or more items of food comprises using a lookup table.

* * * * *